(12) United States Patent
Hansson

(10) Patent No.: US 7,517,218 B2
(45) Date of Patent: *Apr. 14, 2009

(54) IMPLANT HAVING CIRCUMFERENTIALLY ORIENTED ROUGHNESS

(75) Inventor: Stig Hansson, Askim (SE)

(73) Assignee: Astra Tech AB, Molndal (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/828,402

(22) Filed: Jul. 26, 2007

(65) Prior Publication Data

US 2008/0038693 A1 Feb. 14, 2008

Related U.S. Application Data

(60) Division of application No. 10/361,383, filed on Feb. 10, 2003, now Pat. No. 7,264,470, which is a continuation of application No. 09/402,918, filed as application No. PCT/SE99/01272 on Jul. 14, 1999, now Pat. No. 6,547,564.

(30) Foreign Application Priority Data

Jul. 17, 1998 (SE) .................................... 9802571

(51) Int. Cl.
*A61C 8/00* (2006.01)
(52) U.S. Cl. ........................................ 433/174; 433/173
(58) Field of Classification Search ......... 433/173–174; D24/156
See application file for complete search history.

(56) References Cited

U.S. PATENT DOCUMENTS 3,466,748 A 9/1969 Christensen (Continued)

FOREIGN PATENT DOCUMENTS

DE 24 13 883 9/1975

(Continued)

OTHER PUBLICATIONS

A. Al-Sayyed, D.A. Deporter, R.M. Pilliar, P.A. Watson, M. Pharoah, K. Berhane, and S. Carter; "Predictable crestal bone remodelling around two porous-coated titanium alloy dental implant designs"; Clinical Oral Implant Research; 1994; pp. 131-141; vol. 5; Munksgaard; Denmark.

(Continued)

*Primary Examiner*—John J Wilson
*Assistant Examiner*—Hao D Mai
(74) *Attorney, Agent, or Firm*—Finnegan, Henderson, Farabow, Garrett & Dunner, LLP

(57) ABSTRACT

Implant (10) having a shaft which is adapted in use to be embedded in bone tissue and which has an outer surface provided with a circumferentially-oriented roughness. The circumferentially-oriented roughness has first and second axial sections (19, 21) with each section comprising a series of circumferentially-oriented peaks which have a crest and which are axially spaced apart by troughs. The axial spacing (d) between the crests of adjacent peaks in the first axial section (19) is less than the axial spacing (3*d*) between the crests of adjacent peaks in the second axial section (21). Although the axial spacing between the crests of adjacent peaks in the first and second axial sections of circumferentially-oriented roughness differs, the first and second axial sections of circumferentially-oriented roughness are adapted in use to provide the same or substantially the same pitch.

28 Claims, 5 Drawing Sheets

U.S. PATENT DOCUMENTS

| | | | |
|---|---|---|---|
| 4,103,422 | A | 8/1978 | Weiss et al. |
| 4,229,169 | A | 10/1980 | Smith et al. |
| 4,416,629 | A | 11/1983 | Mozsary et al. |
| 4,463,753 | A | 8/1984 | Gustilo |
| 4,468,200 | A | 8/1984 | Münch |
| 4,624,673 | A | 11/1986 | Meyer |
| 4,713,004 | A | 12/1987 | Linkow et al. |
| 4,723,913 | A | 2/1988 | Bergman |
| 4,772,204 | A | 9/1988 | Soderberg |
| 4,781,591 | A | 11/1988 | Allen |
| 4,790,753 | A | 12/1988 | Fradera |
| 4,826,434 | A | 5/1989 | Krueger |
| 4,854,311 | A | 8/1989 | Steffee |
| 4,932,868 | A | 6/1990 | Linkow et al. |
| 4,960,381 | A | 10/1990 | Niznick |
| 4,976,739 | A | 12/1990 | Duthie, Jr. |
| 4,988,299 | A | 1/1991 | Branemark |
| 5,000,686 | A | 3/1991 | Lazzara et al. |
| 5,007,835 | A | 4/1991 | Valen |
| 5,022,860 | A | 6/1991 | Lazzara et al. |
| 5,035,619 | A | 7/1991 | Daftary |
| 5,061,181 | A | 10/1991 | Niznick |
| 5,073,111 | A | 12/1991 | Daftary |
| 5,076,788 | A | 12/1991 | Niznick |
| 5,078,607 | A | 1/1992 | Niznick |
| 5,087,199 | A | 2/1992 | Lazarof |
| 5,145,372 | A | 9/1992 | Daftary et al. |
| 5,199,873 | A | 4/1993 | Schulte et al. |
| 5,209,659 | A * | 5/1993 | Friedman et al. ............ 433/173 |
| 5,213,502 | A | 5/1993 | Daftary |
| 5,259,398 | A | 11/1993 | Vrespa |
| 5,290,171 | A | 3/1994 | Daftary et al. |
| 5,297,963 | A | 3/1994 | Daftary |
| 5,302,126 | A | 4/1994 | Wimmer |
| 5,310,343 | A | 5/1994 | Hasegawa et al. |
| 5,344,457 | A | 9/1994 | Pilliar et al. |
| 5,360,452 | A | 11/1994 | Engelhardt et al. |
| 5,362,235 | A | 11/1994 | Daftary |
| 5,362,236 | A | 11/1994 | Bränemark |
| 5,376,004 | A | 12/1994 | Mena |
| 5,403,136 | A | 4/1995 | Mathys |
| 5,417,568 | A | 5/1995 | Giglio |
| 5,427,527 | A | 6/1995 | Niznick et al. |
| 5,431,567 | A | 7/1995 | Daftary |
| 5,435,723 | A | 7/1995 | O'Brien |
| 5,456,723 | A | 10/1995 | Steinemann et al. |
| 5,470,230 | A | 11/1995 | Daftary et al. |
| 5,476,382 | A | 12/1995 | Daftary |
| 5,527,182 | A | 6/1996 | Willoughby |
| 5,527,183 | A | 6/1996 | O'Brien |
| 5,547,377 | A | 8/1996 | Daftary |
| 5,571,017 | A | 11/1996 | Niznick |
| 5,588,838 | A * | 12/1996 | Hansson et al. ............ 433/173 |
| 5,601,429 | A | 2/1997 | Blacklock |
| 5,601,553 | A | 2/1997 | Trebing et al. |
| 5,607,428 | A | 3/1997 | Lin |
| 5,639,237 | A | 6/1997 | Fontenot |
| 5,642,996 | A | 7/1997 | Mochida et al. |
| 5,695,336 | A | 12/1997 | Lazzara et al. |
| 5,727,943 | A | 3/1998 | Beaty et al. |
| 5,759,034 | A | 6/1998 | Daftary |
| 5,769,850 | A | 6/1998 | Chin |
| 5,795,160 | A | 8/1998 | Hahn et al. |
| 5,810,592 | A | 9/1998 | Daftary |
| D401,694 | S | 11/1998 | Daftary |
| D401,695 | S | 11/1998 | Daftary |
| 5,915,967 | A | 6/1999 | Crokie |
| 5,954,722 | A | 9/1999 | Bono |
| 5,976,142 | A | 11/1999 | Chin |
| 6,036,693 | A | 3/2000 | Yuan et al. |
| 6,045,554 | A | 4/2000 | Grooms et al. |
| 6,129,548 | A | 10/2000 | Lazzara et al. |
| 6,129,728 | A | 10/2000 | Schumacher et al. |
| 6,231,606 | B1 | 5/2001 | Graf et al. |
| 6,299,615 | B1 | 10/2001 | Huebner |
| 6,321,606 | B1 | 11/2001 | Ishii et al. |
| D455,833 | S | 4/2002 | Daftary |
| D456,900 | S | 5/2002 | Daftary |
| D470,939 | S | 2/2003 | Daftary |
| 6,547,564 | B1 | 4/2003 | Hansson |
| 6,565,357 | B1 | 5/2003 | Lazzara et al. |
| 6,651,961 | B1 | 11/2003 | Meyer |
| 6,655,961 | B2 | 12/2003 | Cottrell |
| 6,672,872 | B2 | 1/2004 | Cottrell |
| 6,672,873 | B2 | 1/2004 | Rubin |
| 2008/0020344 | A1 | 1/2008 | Hansson |
| 2008/0020345 | A1 | 1/2008 | Hansson |
| 2008/0020346 | A1 | 1/2008 | Hansson |
| 2008/0020347 | A1 | 1/2008 | Hansson |
| 2008/0020348 | A1 | 1/2008 | Hansson |

FOREIGN PATENT DOCUMENTS

| | | |
|---|---|---|
| DE | 37 11 884 A1 | 10/1988 |
| DE | 41 30 891 A1 | 3/1992 |
| DE | 43 32 075 A1 | 3/1994 |
| EP | 0 291 103 B1 | 11/1988 |
| EP | 0 323 421 A2 | 7/1989 |
| EP | 0 388 576 A1 | 9/1990 |
| EP | 0 424 734 A1 | 5/1991 |
| EP | 0 438 984 A1 | 7/1991 |
| EP | 0438 048 B1 | 5/1994 |
| JP | 03-176045 A | 7/1991 |
| JP | 04-231042 A | 8/1992 |
| TW | 239291 | 1/1995 |
| WO | WO 89/03200 A1 | 4/1989 |
| WO | WO 94/07428 A1 | 4/1994 |
| WO | WO 94/09717 A1 | 5/1994 |
| WO | WO 94/17750 A1 | 8/1994 |
| WO | WO 97/29713 A1 | 8/1997 |
| WO | WO 97/43976 A1 | 11/1997 |
| WO | WO 00/03656 A1 | 1/2000 |
| WO | WO 00/03657 A1 | 1/2000 |
| WO | WO 03/015654 A1 | 2/2003 |

OTHER PUBLICATIONS

Bernt Andersson; "Implants for Single-Tooth Replacement: A clinical and experimental study on the Branemark CeraOne System"; Swedish Dental Journal; May 24, 1995; pp. 1-41; supplement 108; Goteborg 1995.

John E.A. Bertram and Sharon M. Swartz; "The 'Law of Bone Transformation': A Case of Crying Wolff?"; Biological Review; 1991; pp. 245-273; vol. 66; Great Britain.

B Engquist, H. Nilson, and P. Astrand; "Single-tooth replacement by osseointegrated Branemark implants"; Clinical Oral Implants Research; 1995; pp. 238-245; vol. 6; Munksgaard; Denmark.

Young-Chul Jung, Chong-Hyun Han, and Keun-Woo Lee; "A 1-Year Radiographic Evaluation of Marginal Bone Around Dental Implants"; The International Journal of Oral & Maxillofacial Implants; 1996; pp. 811-818; vol. 11, No. 6.

Ch. Malevez, M. Hermans, and Ph. Daelemans; "Marginal bone levels at Branemark system implants used for single tooth restoration. The influence of implant design and anatomical region"; Clinical Oral Implants Research; 1996; pp. 162-169; vol. 7; Munksgaard; Denmark.

R.M. Palmer, B.J. Smith, P.J. Palmer, and P.D. Floyd; "A prospective study of Astra single tooth implants"; Clinical Oral Implants Research; 1997; pp. 173-179; vol. 8; Munksgaard; Denmark.

M. Quirynen, I. Naert, and D. Van Steenberghe; "Fixture design and overload influence marginal bone loss and fixture success in the Branemark system"; Clinical Oral Implants Research; Sep. 1992; pp. 104-111; vol. 3, No. 3; Munksgaard; Denmark.

Helene Vaillan Court, Robert M. Pilliar, and Derek McCammond; "Factors Affecting Crestal Bone Loss With Dental Implants Partially Covered With a Porous Coating: A Finite Element Analysis"; The International Journal of Oral & Maxillofacial Implants; 1996; pp. 351-359; vol. 11.

H. Vaillan Court, R.M. Pilliar, and D. McCammond; "Factors Affecting Crestal Bone Loss around Porous-Coated Dental Implants"; Journal of Applied Biomaterials; 1995; pp. 267-282; vol. 6.

Stig Hansson; "Toward an Optimized Dental Implant and Implant Bridge Design: A Biomechanical Approach"; Doctoral thesis for the degree of Doctor of Philosophy, Biomechanics, Department of Polymeric Materials, School of Mechanical and Vehicular Engineering, Chalmers University of Technology, S-412 96 Goteborg Sweden; 1997.

Beatrice Stoiber: "Biomecahnische Grundlagen Enossaler Schraubenimplantate"; 1988; Universitatsbibiiothek Wien.

Notice of Opposition to a European Patent, filed on Sep. 5, 2007, in corresponding European Patent No. 1098606 (Application No. 99941924.5).

Notice of Opposition to a European Patent, filed on Aug. 24, 2007, in corresponding European Patent No. 1098606 (Application No. 99941924.5).

Response to Communication of Notice of Opposition R.57(1) EPC, filed with the European Patent Office on Apr. 25, 2008, for counterpart European Patent No. 1 098 606 B9 (26 pages).

* cited by examiner

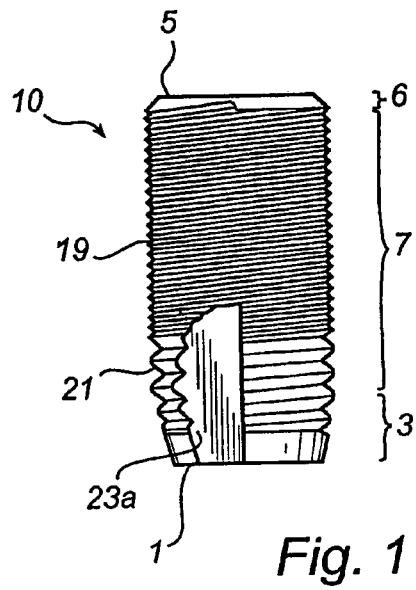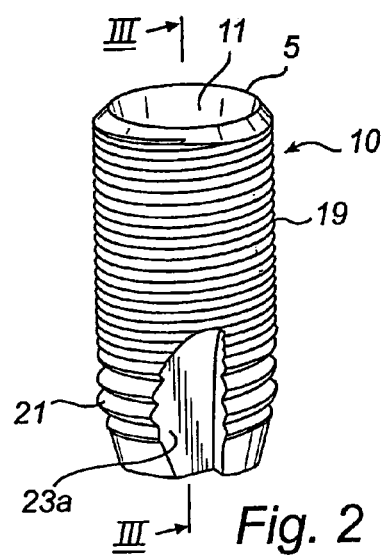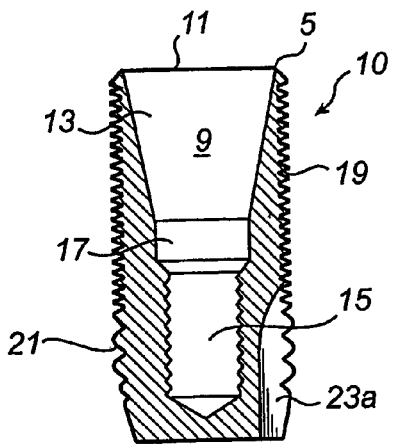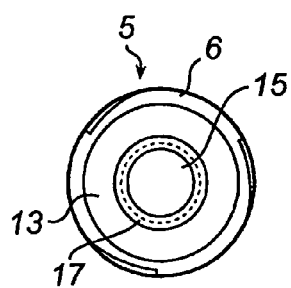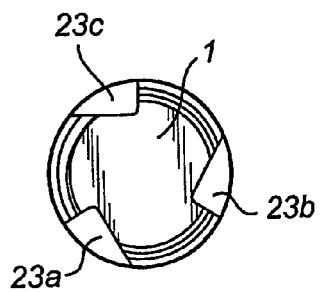

IMPLANT HAVING CIRCUMFERENTIALLY ORIENTED ROUGHNESS

CROSS-REFERENCE TO RELATED APPLICATIONS

This is a divisional application of U.S. patent application Ser. No. 10/361,383, filed Feb. 10, 2003, now pending; which is a continuation application of U.S. patent application Ser. No. 09/402,918, filed Oct. 13, 1999, now U.S. Pat. No. 6,547,564; which is a 371 of International Patent Application No. PCT/SE99/01272, filed Jul. 14, 1999, now abandoned; and claims the benefit of Swedish Application No. 9802571-1, filed Jul. 17, 1998, the entirety of all of which are incorporated herein by reference.

FIELD OF THE INVENTION

The present invention relates to an implant having a shaft which is adapted in use to be embedded in bone tissue and which has an outer surface provided with a circumferentially-oriented roughness. This will hereinafter be referred to as an "implant of the type defined".

BACKGROUND OF THE INVENTION

Implants of the type defined are known for use as the anchoring members of dental and orthopaedic prostheses. To this end, the implant is inserted into a bore-hole drilled into the bone tissue of a bone tissue structure at a site where a prosthesis is required, ordinarily by screwing of the implant into the bore-hole. The convention in the art is for the circumferentially-oriented roughness to take the form of a screw thread and in this case the bore-hole will ordinarily be (i) provided with internal threads in advance, or (ii) left untapped with the implant being provided with a self-tapping capacity, e.g. by the provision of one or more axially-extending cutting recesses or notches in the screw thread.

A superstructure having the prosthetic part of the prosthesis is then secured to the implant. In the case of a dental prosthesis, the superstructure will typically consist of a spacer or transmucosal component which engages to the implant to bridge the gingiva overlying the maxilla or mandible at the implant site and the prosthetic part, e.g. a crown, bridge or denture, is then secured to the spacer. There are various other forms that the superstructure can take as is known in the art. For instance, the prosthetic part may be secured directly to the implant.

The long-term integrity of the prosthesis is highly dependent on the successful osseointegration of the implant with the bone tissue structure, that is to say, the remodelling of the bone tissue in the bone tissue structure into direct apposition with the implant. A study on the factors which affect the osseointegration of implants was undertaken by Professor Per-Ingvar Brånemark and co-workers and the results were published in a book entitled "*Osseointegrated Implants in the Treatment of the Edentulous Jaw: Experience from a 10-Year Period*", Almqvist & Wiskell International, Stockholm, Sweden, 1977. It was found by Brånemark et al that successful osseointegration depends upon inter alia the use of biocompatible materials for the implant, for example titanium and alloys thereof, and the surgical procedure adopted, for example leaving the implant unloaded for several months before adding the superstructure.

Implants of the type defined are not necessarily always used as part of a prosthesis, in some instances they can be a "stand alone" structure. As an example, implants of the type defined are known for use as bone fixation screws. The success of these "stand alone" implants is also highly dependent on their successful osseointegration.

Implants of the type defined have some notable advantages in promoting successful osseointegration with the adjacent bone tissue, a major one being as a result of the fact that the main loads on the implant in the clinical situation are axial loads. These implants are very well suited to support axial loads and this may be particularly important in the initial stages of the osseointegration process in which it is important that the implant is fully stable and as immovable as possible in the borehole (primary fixation). One can consider this to be due to the bone tissue growing into the troughs between adjacent peaks of the circumferentially-oriented roughness on the implant.

The Applicant has also identified that it is advantageous for an implant of the type defined to transmit the axial loading thereon evenly to the adjacent bone tissue to prevent high stress concentrations occurring in the adjacent bone tissue and concomitantly marginal bone tissue resorption. If marginal bone tissue resorption occurs this will reduce the anchorage of the implant and may undermined the long-term stability of the implant resulting in due course in failure of the prosthesis. In the particular case of dental prostheses, the aesthetic appeal is also undermined by marginal bone tissue resorption, an important drawback since dental prosthetics forms part of the field of cosmetic surgery.

The present invention proposes to provide an implant of the type defined having features which promote its maintenance in a bone tissue structure whilst at the same time facilitating its insertion into the bone tissue structure in the first place.

SUMMARY OF THE INVENTION

According to the present invention there is provided an implant of the type defied in which the circumferentially-oriented roughness has first and second axial sections each comprising a series of circumferentially-oriented peaks which have a crest and which are axially spaced apart by troughs, the axial spacing between the crests of adjacent peaks in the first axial section is less than the axial spacing between the crests of adjacent peaks in the second axial section and the first and second axial sections of circumferentially-oriented roughness are adapted in use to provide the same or substantially the same pitch.

The larger inter-peak spacing in the second axial section of circumferentially-oriented roughness acts to promote primary fixation of the implant in the bone tissue during the early phases of osseointegration since each trough between adjacent peaks can capture a relatively large volume of bone tissue to interlock the implant with the bone tissue. The smaller inter-peak spacing in the first axial section, on the other hand, enables the stiffness of the implant to be increased thereby improving the ability of the implant to transmit loads more evenly to the bone tissue to inhibit marginal bone resorption. Adapting the first and second axial sections to have the same or substantially the same pitch means that both axial sections produce the same or substantially the same axial displacement into the bone tissue on one rotation thereof thus ensuring that the provision of the two different axial sections of circumferentially-oriented roughness does not complicate insertion of the implant into the bone tissue. If the first and second axial sections of circumferentially-oriented roughness did not have the same or substantially the same pitch then a greater force would need to be applied to insert the implant resulting in fractures being formed in the bone tissue.

In an embodiment of the invention such as the one hereinafter to be described the pitch is a predetermined distance, the ratio of the predetermined distance to the axial spacing between the crests of adjacent peaks in the first axial section is a first multiple integer and the ratio of the predetermined distance to the axial spacing between the crests of adjacent peaks in the second axial section is a second multiple integer which is less than the first multiple integer. The first multiple integer may be a multiple integer of the second multiple integer.

In an embodiment of the invention such as the one hereinafter to be described the peaks in the first and second axial sections are circumferentially-oriented at a common inclined angle to the main axis of the implant.

In an embodiment of the invention such as the one hereinafter to be described the shaft has a coronal end and an apical end and the first axial section is located coronally of the second axial section.

In an embodiment of the invention such as the one hereinafter to be described the first and second axial sections are contiguous.

In an embodiment of the invention such as the one hereinafter to be described the first axial section extends from the coronal end of the shaft to a position coronally of the apical end and the second axial section extends from the first axial section towards the apical end of the shaft. The implant may have a coronal end which is spaced coronally from the coronal end of the shaft by a smooth coronal portion of the implant, as in the embodiment of the invention hereinafter to be described, in which case the smooth coronal portion is preferably no more than 4% of the total length of the implant, more preferably in the range 1.5-3.7% of said total length.

In an embodiment of the invention such as the one hereinafter to be described the axial extent of the first axial section is greater than the axial extent of the second axial section. Alternatively, the axial extent of the first axial section may be less than the axial extent of the second axial section or the axial extents of the first and is second axial sections may be the same or substantially the same.

In an embodiment of the invention in which the first axial section is disposed coronally of the second axial section, such as the one hereinafter to be described, a blind bore extends apically into the shaft from the coronal end thereof to an end surface in-between the apical and coronal ends of the shaft for a superstructure to be secured to the implant, the blind bore comprising an internally-threaded section having a coronal edge and an apical edge for screw connection of the superstructure to the implant with the apical edge terminating at a position which is disposed apically of the first axial section. Alternately, the apical edge of the internally-threaded section of the blind bore may terminate at a position which is disposed coronally of the second axial section. The internally-threaded section may be an apical section of the blind bore, as in the embodiment of the invention hereinafter to be described.

In an embodiment of the invention such as the one hereinafter to be described all or substantially all of the crests of the peaks in the first and second axial sections lie on an axial plane parallel to the main axis of the shaft. Expressed another way, the major transverse dimension of the implant at the first and second axial sections is uniform.

In an embodiment of the invention such as the one hereinafter to be described the height of the peaks, as measured from the troughs to the crests, in the first axial section differs from that in the second axial section. To advantage, the height of the peaks in the first axial section is less than that in the second axial section. This feature further enables the stiffness of the implant to be increased.

In an alternative embodiment of the invention the height of the peaks, as measured from the troughs to the crests, in the first axial section is the same or substantially the same as in the second axial section.

In an embodiment of the invention such as the one hereinafter to be described the ratio of the height of the peaks, as measured from the troughs to the crests, to the axial spacing between the crests of adjacent peaks in the first axial section is the same or substantially the same as in the second axial section.

In an embodiment of the invention such as the one hereinafter to be described the height of the peaks, as measured from the troughs to the crests, in the first axial section is no greater than 0.2 mm, for example in the range 0.02-0.20 mm, and the height of the peaks, as measured from the troughs to the crests, in the second axial section is greater than that in the first axial section, for instance in the range 0.15 mm to 1 mm. Such heights complement the primary fixation and stiffness characteristics of the implant provided by the different inter-peak spacings of the first and second axial sections.

In an embodiment of the invention such as the one hereinafter to be described the peaks in the first and second axial sections are bounded by flank surfaces and the angle between the opposed flanks of adjacent peaks in the first and second axial sections is the same.

In an embodiment of the invention such as the one hereinafter to be described the troughs in at least one of the first and second axial sections are a continuous curved surface.

In an embodiment of the invention such as the one hereinafter to be described the circumferentially-oriented roughness in the first and/or second axial section is presented by a screw thread profile with the circumferentially-oriented peaks being defined by thread elements of the screw thread profile.

Typically, the screw thread profile of the first and/or second axial section will be formed by a screw thread structure. In such case, the screw thread structure of the first axial section may be formed by a first set of independent screw threads each having turns; the turns of each independent screw thread in the first set defining thread elements in the first axial section and being sequentially arranged with the turns of the other independent screw threads in the first set with adjacent turns of one of the independent screw threads of the first set being axially-spaced apart by a predetermined spacing distance which is the same for adjacent turns of the other independent screw threads in the first set; and the screw thread structure of the second axial section may be formed by (i) an independent screw thread having turns which define the thread elements of the second axial section and are axially-spaced apart by the predetermined spacing distance or essentially the predetermined spacing distance, or (ii) a second set of independent screw threads numbering less than in the first set each having turns, the urns of each independent screw thread in the second set defining thread elements in the second axial section and being sequentially arranged with the turns of the other independent screw threads in the second set with adjacent turns of each independent screw thread of the second set being axially-spaced apart by the predetermined spacing distance or essentially the predetermined spacing distance.

In an embodiment of the invention one or more of the independent screw threads of the first and second axial sections are shared by the first and second axial sections.

In an embodiment of the invention such as the one hereinafter to be described the or each independent screw thread of at least one of the first and second axial sections is a microthread, that is to say, a thread having a height which is no greater than 0.2 mm.

In an embodiment of the invention only the screw threads of the first axial section are microthreads. It could be the case, though, that the screw threads of both the first and second axial sections are microthreads.

In an embodiment of the invention the circumferentially-oriented roughness in at least one of the first and second axial sections is formed by a series of axially spaced-apart circumferential lines of beads. The beads in each line may be circumferentially spaced-apart.

In an embodiment of the invention such as the one hereinafter to be described the implant is a dental implant adapted for implantation in the maxilla or mandible of an edentulous patient for supporting a superstructure which presents one or more artificial teeth.

According to the invention there is further provided a method of implanting an implant into a bone tissue structure comprising the steps of providing an implant according to the invention, providing a bore-hole in the bone tissue structure and screwing the implant into the bore-hole so that the shaft is embedded in the bone tissue.

BRIEF DESCRIPTION OF THE DRAWINGS

By way of example, a self-tapping endosseous screw-type dental implant in accordance with the present invention will now be described with reference to the accompanying Figures of drawings in which:

FIG. 1 is a side view of the dental implant;

FIG. 2 is a perspective view of the dental implant;

FIG. 3 is a cross-sectional side view of the dental implant;

FIG. 4 is a plan view of the dental implant;

FIG. 5 is an underneath view of the dental implant;

DESCRIPTION OF EXEMPLARY EMBODIMENT OF THE INVENTION

Figure 6:
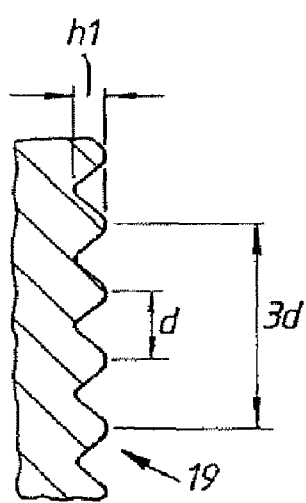
FIG. 6 is an exploded view of a first section of the external screw threading on the dental implant.

In the accompanying Figures of drawings there is shown various views of a self-tapping endosseous screw-type dental implant 10 of a dental prosthesis in accordance with the present invention. The implant 10 is for insertion into a bore-hole drilled into a toothless-site in a maxilla or mandible of a partially or fully edentulous patient to anchor to the maxilla or mandible a superstructure of the prosthesis which comprises a prosthetic part, namely one or more artificial teeth. The implant 10 is made from commercially pure titanium, a titanium alloy, another biocompatible metal or metal alloy or a ceramic to promote osseointegration of the implant with the bone tissue of the boundary walls of the bore-hole.

Referring to FIG. 1, the implant 10 has an apical end 1 which is presented by a first conical section 3 to ease insertion of the implant 10 into the bore-hole, a coronal end 5 presented by a second conical section 6 and an intermediate section 7 of constant diameter which extends between the first and second conical sections 3, 6.

The length of the implant may be in the range 8-19 mm, depending on the clinical situation, and have a maximum outer diameter of 3.5 mm or 4.0 mm. The axial extent of the second conical portion 6 is preferably small compared to the total length of the implant 10, as an example no more than 4.0% perhaps in the range 1.5%-73.7%.

Turning to FIGS. 2 to 4, a socket 9 having an open end 11 in the coronal end 5 extends apically into the implant 10. The socket 9 is for receiving an abutment structure (not shown) which will bridge the gingiva overlying the bore-hole and support/present the prosthetic part. The socket 9 consists of a conical coronal section 13, an internally-threaded apical section 15 and a cylindrical intermediate section 17. The abutment structure will have an apical section which is able to be screw retained in the implant socket 9 for releasably securing the abutment structure to the implant 10.

As shown in FIGS. 1 to 3, 6 and 7, the outer surface of the implant 10 over the major part of its length is provided with screw threading which is divided into coronal and apical sections 19, 21 having different thread heights h1, h2. As shown most clearly in FIG. 1, the coronal section 19 of screw threading is positioned on the intermediate cylindrical section 7 of the implant 10 whereas the apical section 21 of the screw threading bridges the intermediate cylindrical section 7 and the first conical section 3.

Referring to FIG. 6, the screw threading in the coronal section 19 is composed of a series of axially spaced-apart screw thread elements each having the same height h1. These screw thread elements are formed by the turns of three separate microthreads (triple microthread) which are sequentially arranged. This means that a screw thread element formed by a first turn of one of the microthreads is axially spaced from a screw thread element formed by the next turn of that microthread by two other screw thread elements, each being respectively formed by a turn of the other two microthreads. A screw thread element belonging to one of the microthreads is therefore axially spaced from the next adjacent screw thread element formed by the same microthread by screw thread elements from each of the other two microthreads. By "microthread" is meant a screw thread having a height which is no greater than 0.2 mm. Accordingly, the screw thread elements in the coronal section 19 have a height h1 which is no greater than 0.2 mm, preferably 0.1 mm.

Figure 7:
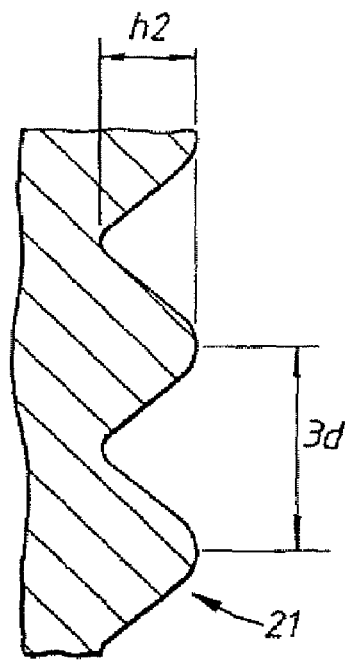
FIG. 7 is an exploded view of a second section of the external screw threading on the dental implant.
Figure 8:
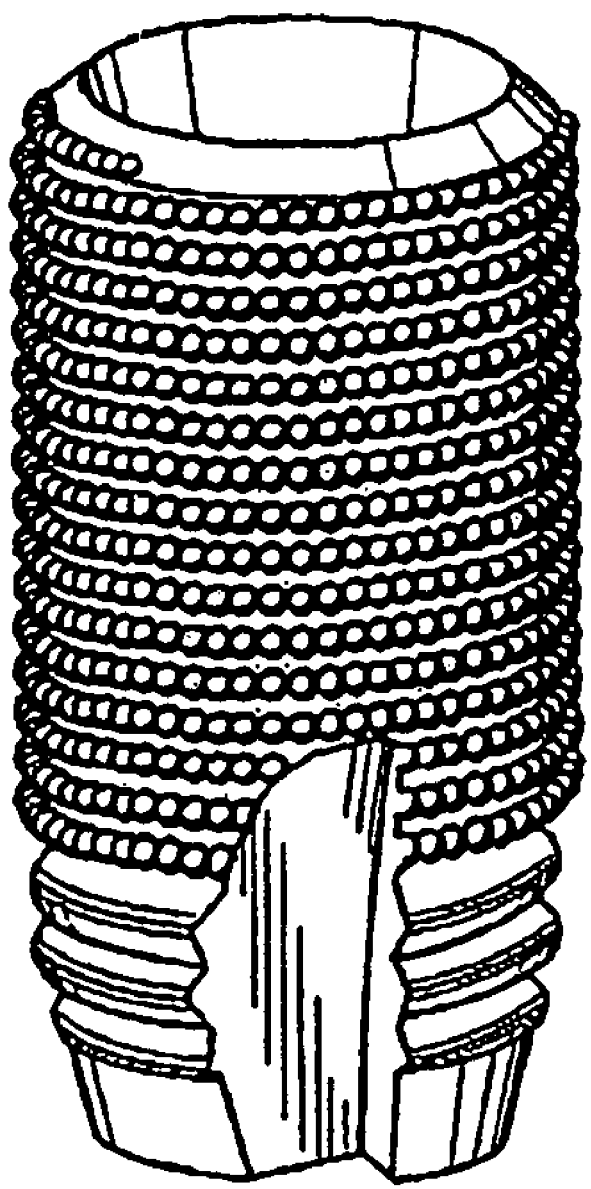
FIG. 8 is a perspective view of a dental implant having circumferentially-oriented roughness consisting of axially spaced, circumferential lines of beads.
Figure 9:
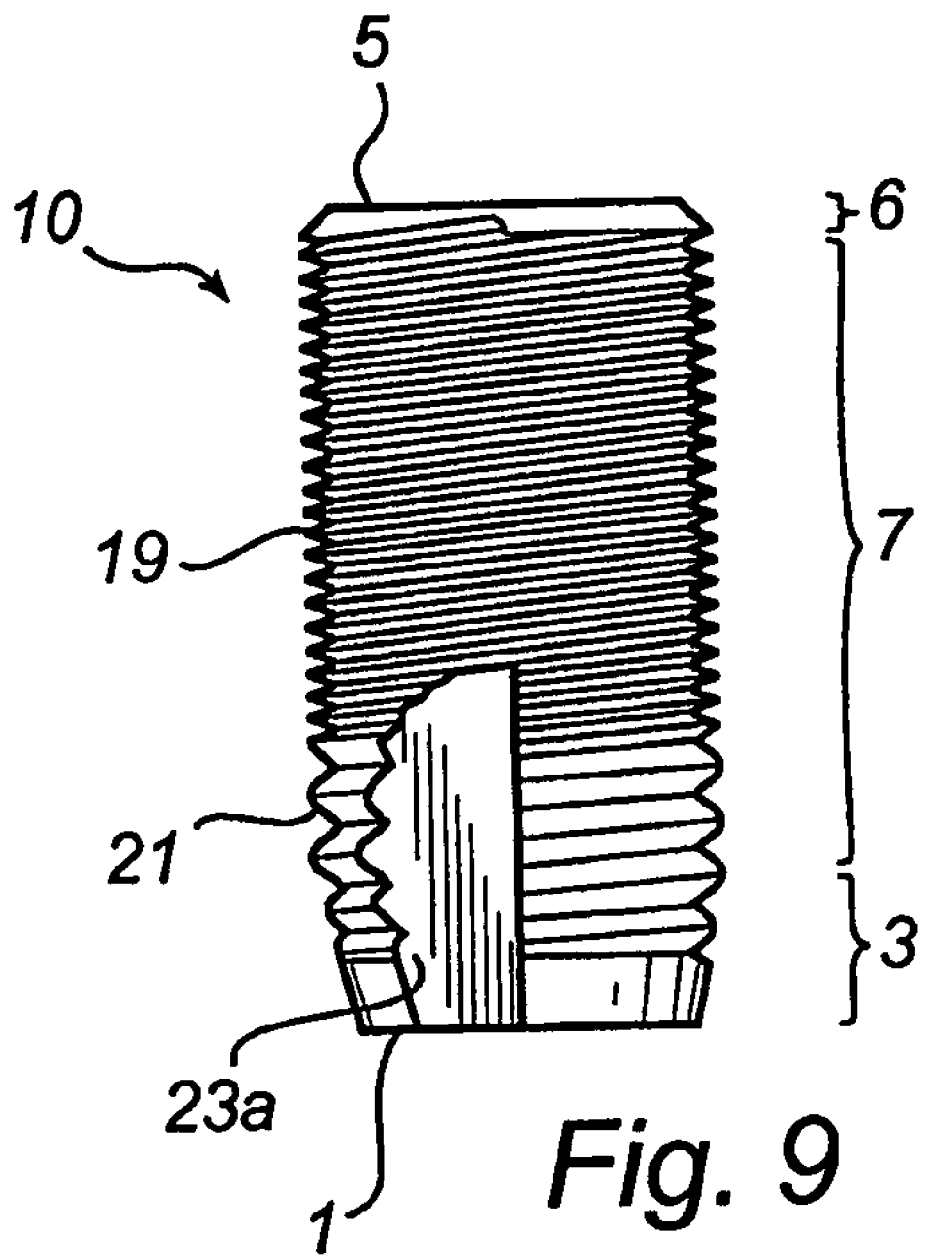
FIG. 9 is a perspective view of a dental implant having circumferentially-oriented roughness in which the height of the peaks in the first axial section and the height of the peaks in the second axial section is the same.
Figure 10:
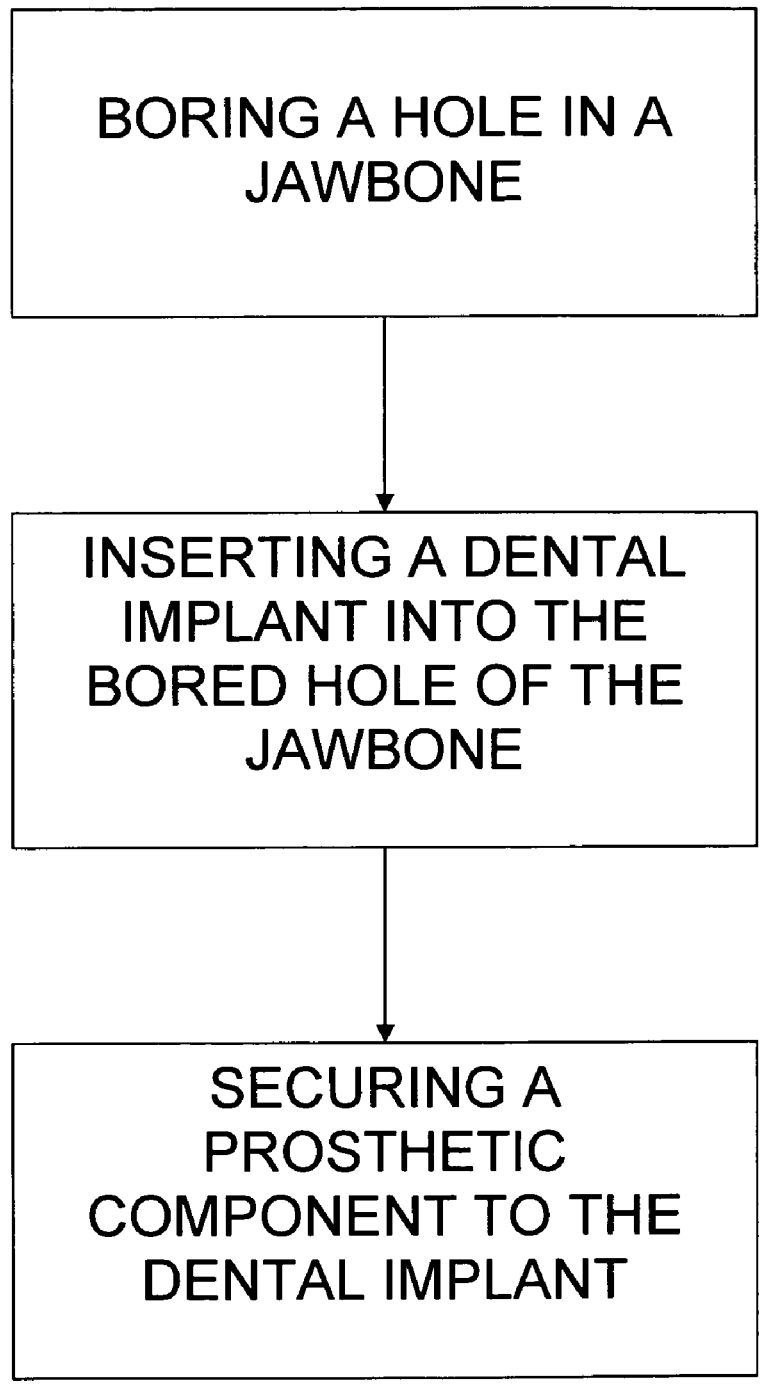
FIG. 10 is a flow chart illustrating an exemplary method of implanting a dental implant into a jawbone.

Referring to FIG. 7, the screw threading in the apical section 21 is composed of a series of axially spaced-apart screw thread elements which, other than those in the first conical section 3, each have the same height h2. The screw thread elements of the apical section 21 are formed by the turns of a single macrothread. By "macrothread" is meant a screw thread having a height greater than 0.2 mm. Accordingly, the screw thread elements of the apical section 21 on the intermediate section 7 have a height greater than 0.2 mm, preferably 0.3 mm.

The angle formed between the coronal and apical flanks of adjacent screw thread elements is the same in both the coronal and apical sections 19, 21. Preferably the angle formed is 80°. It will also be noted from FIGS. 6 and 7 that the coronal and apical flanks of adjacent screw thread elements in the coronal and apical sections 19, 21 are connected by a curved surface, that is to say, there is no axial straight part in-between adjacent screw thread elements in the coronal and apical sections 19, 21.

As can be seen particularly from FIGS. 1 and 3, the tips of the screw thread elements of the coronal section 19 and the tips of the screw thread elements of the apical section 21 positioned in the intermediate cylindrical section 7 of the implant 10 all lie on a common plane when viewed in side section and circumscribe the circumference of the cylindrical intermediate section 7. In other words, the major diameter of the intermediate cylindrical section 7 is constant.

As shown in FIGS. 6 and 7, as well as the screw thread elements in the coronal and apical sections 19, 21 having different heights from one another the crest-to-crest spacing between adjacent screw thread elements in the coronal section 19 is different from the crest-to-crest spacing between adjacent screw thread elements in the apical section 21. The crest-to-crest spacing in the coronal section 19 is d whereas the crest-to-crest spacing in the apical section 21 is 3d. As an example, d may be 0.22 mm. In the case where h1 is 0.1 mm and h2 is 0.3 mm the ratio of the inter-crest spacing to the height would thus be the same for both the coronal and apical threaded sections 19, 21, namely d/h1=2.2=3d/h2.

It follows from the above that the crest-to-crest spacing between adjacent screw thread elements of each microthread is the same as that between adjacent screw thread elements of the macrothread, namely 3d. The fact that the crest-to-crest spacing between adjacent screw thread elements per se in the coronal section 19 is less than that in the apical section 21 is, of course, due to adjacent turns of each microthread being interspersed with a turn from each of the other two microthreads. It will also be noted from FIG. 1 that the turns of the microthreads and the macrothreads are aligned parallel with one another at an inclined angle to the rotational axis of the implant 10.

It will be gathered from the above that the pitch of the coronal and apical threaded sections, 19, 21 will be the same, again being 3d. For this reason, the pitch of the implant 10 remains uniform along its length notwithstanding the difference in crest-to-crest spacing in the apical and coronal threaded sections 19, 21, that is to say, the coronal and apical screw threaded sections 19, 21 will both produce the same axial displacement of the implant 10 when being screwed into the bore-hole provided therefor at the toothless site in the maxilla or mandible. If the coronal and apical sections 19, 21 did not have constant pitch then a greater force would need to be applied to insert the implant 10 into the bore-hole resulting in bone threads formed in the boundary wall of the bore-hole being fractured.

As a rule, a constant pitch for two threaded sections having different crest-to-crest spacings between the adjacent screw thread elements thereof will result where the first threaded section is formed by the sequential arrangement of the turns of a first set of screw threads each having the same pitch and the second threaded section is formed by (i) a single screw thread having the same pitch as the screw threads in the first threaded section, or (ii) the sequential arrangement of the turns of a second set of screw threads numbering less than in the first set each having the same pitch as the screw threads in the first threaded section. The number of screw threads in the first threaded section does not need to be a multiple integer of the number of screw threads in the second threaded section, as in the illustrated embodiment of the invention. For example, there could be five microthreads in the coronal section 19 and two macrothreads in the apical section 21.

As shown in FIGS. 1 to 3 and 5, the implant 10 has three cutting recesses or grooves 23a, 23b, 23c positioned symmetrically about the circumference of the apical end 1 of the implant 10 for self-tapping of the implant to when being screwed into the bore-hole provided therefor in the maxilla or mandible.

In use, the implant 10 is screwed into the bore-hole provided at the toothless-site in the maxilla or mandible such that the coronal and apical sections 19, 21 are embedded in bone tissue with the second conical section 6 protruding from the maxilla or mandible. The screw thread elements of the macrothreads in the apical section 21 of the implant 10 act to provide primary fixation of the implant in the bore-hole. The screw thread elements of the microthreads in the coronal section 19 also act to provide fixation for the implant 10 in the bore-hole. As a result of the screw threads in the coronal section 19 being microthreads, though, the implant 10 is stiffer than it would be if the screw threads were macrothreads as in the apical section 21. This enables the implant 10 to transfer loads more evenly to the bone tissue adjacent the implant 10 and consequently promote better remodelling of the bone tissue into apposition with the implant 10. Moreover, as the microthreads are positioned at the coronal end 5 of the implant 10 the loads transferred thereby helps alleviate the problem of bone tissue resorption at the coronal surface of the maxilla or mandible (marginal bone tissue resorption).

The provision of micro threads in the coronal section 19 also enables a reasonable wall thickness to be retained around the tapered coronal section 13 of the socket 9 in the implant 10, when compared to the wall thickness that would result from use of macrothreads in the coronal section 19 in any event. This helps preserve the mechanical strength of the implant 10.

To conclude, the dental implant 10 has a screw threaded outer surface 19, 21 which (i) makes it straightforward for the implant 10 to be screwed into a bone tissue structure, and (ii) promotes the short- and long-term stability of the implant 10 in the bone tissue structure.

It will be appreciated that the invention has been illustrated with reference to an exemplary embodiment and that the invention can be varied in many different ways within the scope of the appended claims. As an example, although the illustrated example is a dental implant the invention has equal application in other areas, for example, the orthopaedic area.

Finally, it is to be noted that the inclusion in the appended claims of reference numerals used in the Figures of drawings is purely for illustrative purposes and not to be construed as having a limiting effect on the scope of the claims.

The invention claimed is:

1. A method of implanting a dental implant into a jawbone, comprising:
  boring a hole in the jawbone;
  inserting into the bored hole of the jawbone the dental implant comprising:
  a shaft having a coronal end, an apical end, and an outer surface provided with a circumferentially-oriented roughness comprising a first axial section and a second axial section, the first axial section being located coronally of the second axial section, and each section of the circumferentially-oriented roughness of the dental implant having a pitch,
  wherein each section of circumferentially-oriented roughness comprises a series of circumferentially-oriented peaks being axially spaced apart by troughs,
  wherein the axial spacing between adjacent peaks in the first axial section is less than the axial spacing between the adjacent peaks of the second axial section,
  wherein the sections of circumferentially-oriented roughness have the same or substantially the same pitch, and
  wherein the dental implant is configured to support one or more artificial teeth.

2. The method of claim 1, wherein the circumferentially-oriented roughness of the first axial section has a height, from trough to crest of the peak, of about 0.2 mm or less.

3. The method of claim 2, wherein inserting the dental implant into the bored hole involves screwing the dental implant into the bored hole.

4. The method of claim 2, wherein inserting the dental implant involves screwing at least some of the circumferentially-oriented peaks of the first and second axial sections into the bored-hole.

5. The method of claim 2, wherein the first and second axial sections are inserted into the bored hole at substantially the same rate.

6. The method of claim 2, further comprising securing a prosthetic component to the dental implant.

7. The method of claim 6, wherein the prosthetic component is selected from the group consisting of a superstructure, a spacer, an abutment structure, a transmucosal component, a crown, a bridge, a denture, one or more artificial teeth, and combinations thereof.

8. The method of claim 6, wherein the prosthetic component includes a prosthetic part selected from the group consisting of at least one of a crown, a bridge, a denture, one or more artificial teeth, and combinations thereof,
wherein the prosthetic component also includes a superstructure selected from the group consisting of at least one of a spacer, an abutment structure, a transmucosal component, and combinations thereof.

9. The method of claim 7, wherein securing the prosthetic component to the dental implant includes securing the prosthetic component to the dental implant via the superstructure.

10. The method of claim 1, wherein the circumferentially oriented roughness of at least one of the first and second axial sections has a series of axially spaced-apart circumferential lines of beads.

11. The method of claim 2, wherein a blind bore extends apically into the shaft from the coronal end to a surface in-between the apical and coronal ends of the shaft,
the method further comprising providing a prosthetic component and placing the prosthetic component in the blind bore.

12. The method of claim 11, wherein the prosthetic component is selected from the group consisting of a superstructure, a spacer, an abutment structure, a transmucosal component, a crown, a bridge, a denture, one or more artificial teeth, and combinations thereof.

13. The method of claim 11, wherein the blind bore comprises an internally-threaded section,
the method further comprising screwing the prosthetic component into the internally-threaded section of the blind bore.

14. The method of claim 2, wherein the circumferentially-oriented roughness of at least one of said first and second sections has a screw thread profile.

15. The method of claim 2, wherein the pitch is a predetermined distance, the ratio of the predetermined distance to the axial spacing between the crests of adjacent peaks in the first axial section is a first multiple integer, the ratio of the predetermined distance to the axial spacing between the crests of adjacent peaks in the second axial section is a second multiple integer and the first multiple integer is greater than the second multiple integer.

16. The method of claim 2, wherein the crests of substantially all of the peaks in the first axial section lie in an axial plane parallel to the main axis of the shaft.

17. The method of claim 2, wherein the crests of substantially all of the peaks in the second axial section lie in an axial plane parallel to the main axis of the shaft.

18. The method of claim 2, wherein substantially all of the crests in the first axial section and the second axial section are configured to be screwed into bone tissue.

19. The method of claim 2, wherein the first axial section is configured to substantially inhibit marginal bone resorption.

20. The method of claim 2, wherein each of the peaks includes a coronal flank and an apical flank,
wherein the coronal flank and the apical flank form an angle of about 80 degrees.

21. The method of claim 2, wherein each of the peaks includes a coronal flank, an apical flank, and a curved portion between the coronal flank and the apical flank.

22. The method of claim 21, wherein the curved portion is disposed between the coronal flank and the apical flank of one peak.

23. The method of claim 2, wherein a height of the peaks, as measured from trough to crest of the peak, of the second axial section is greater than about 0.2 mm.

24. The method of claim 23, wherein the height of the peaks, as measured from trough to crest of the peak, of the second axial section is about 0.3 mm.

25. The method of claim 2, wherein each of the peaks includes a coronal flank and an apical flank,
wherein a portion between the coronal flank and the apical flank of substantially all of the peaks substantially lack sharp edges.

26. The method of claim 2, wherein the axial spacing between adjacent peaks in at least one of the first axial section and the second axial section is between about 0.1 mm and about 0.3 mm.

27. The method of claim 2, wherein the circumferentially-oriented roughness of at least one of said first and second axial sections has a series of axially spaced-apart circumferential lines of beads.

28. The method of claim 2, wherein the first axial section has a cylindrical shape.

* * * * *